United States Patent [19]

Friedman et al.

[11] Patent Number: 4,954,531

[45] Date of Patent: *Sep. 4, 1990

[54] USE OF 2,5-ANHYDRO-D-MANNITOL AS A FOOD INTAKE MODIFIER

[75] Inventors: Mark I. Friedman, Merion; Michael G. Tordoff; Michael J. DiNovi, both of Philadelphia; Robert J. Rafka, Ardmore, all of Pa.

[73] Assignee: Monell Chemical Senses Center, Philadelphia, Pa.

[*] Notice: The portion of the term of this patent subsequent to Feb. 28, 2006 has been disclaimed.

[21] Appl. No.: 231,941

[22] Filed: Aug. 15, 1988

Related U.S. Application Data

[62] Division of Ser. No. 910,698, Sep. 23, 1986, Pat. No. 4,808,626.

[51] Int. Cl.$^5$ .......................................... A61K 31/045
[52] U.S. Cl. ..................................................... 514/738
[58] Field of Search ........................................ 514/738

[56] References Cited

PUBLICATIONS

Kissileff, H. R. et al., "Physiology of the Control of Food Intake", *Ann. Rev. Nutri.*, 2:371–418 (1982).

Russek, M., "Current Status of the Hepatostatic Theory of Food Intake Control", *Appetite*, 2:137–143 (1981).

Friedman, M. I. et al., "The Physiological Psychology of Hunger: A Physiological Perspective", *Physiological Review*, 83(6):409–431 (1976).

Riquelme, P. T. et al., "Mechanism of Action of 2,5-Anhydro-D-Mannitol in Hepatocytes", *Journal of Biological Chemistry*, 259(8):5115–5123 (Apr. 25, 1984).

Stevens, H. C. et al., "2,5-Anhydro Mannito Inhibits Gluconeogenesis from Dihydroxyacetone in Rat Hepatocytes", *Fed. Proc.*, 42, Part 2, Abstract No. 2384 (1983).

Stevens, H. C. et al., "2,5-Anhydro-D-Mannitol Inhibits Glycogenolysis in Isolated Rat Hepatocytes", *Fed. Proc.*, 40, Part 1, Abstract 3479 (1981).

Hanson, R. L. et al., "Hypoglycemic Effect on 2,5-Andro-D-Mannitol", *Fed. Proc.*, 42 (Part 2), Abstract No. 1453 (1983).

Raushel, F. M. et al., "The Substrate and Anomeric Specificity of the Fructokinase", *Journal of Biological Chemistry*, 248(23):8174–8177 (Dec. 10, 1973).

Requelme, P. T. et al., "Inhibition by 2,5-Anhydromannitol of Glycolysis in Isolated Rat Hepatocytes and in Ehrlich Ascites Cells", *Proc. Natl. Acad. Sci. USA*, 82:78–82 (Jan. 1985).

Riquelme, P. T. et al., "Regulation of Carbohydrate Metabolism by 2,5-Anhydro-D-Mannitol", *Proc. Natl. Acad. Sci. USA*, 80:4301–4305 (Jul. 1983).

Hanson, R. L. et al., "Inhibition of Gluconneogenesis and Glycogenolysis by 2,5-Anhydro-Mannitol", *Journal of Biological Chemistry*, 259(1):218–223 (Jan. 10, 1984).

Primary Examiner—Frederick E. Waddell
Attorney, Agent, or Firm—Woodcock Washburn Kurtz Mackiewicz & Norris

[57] ABSTRACT

A novel method for altering the food intake of a mammal is diclosed wherein 2,5-anhydro-D-mannito (2,5-AM) is administered to that mammal in an amount sufficient to alter its food intake. Preferably, normal feeding and fasting periods, and most preferably diurnal feeding and fasting periods, are identified. The mammal receives an intragastric, or intraperitoneal, or intravenous administration within two hours in advance of the onset of the feeding period to decrease food intake, or within two hours of the onset of the fasting period to increase intake. The subject mannitol is preferably administered in amounts of 50–800 mg/kg, although neither the low limit of sufficiency nor the upper limit of activity have yet to be identified.

6 Claims, 4 Drawing Sheets

USE OF 2,5-ANHYDRO-D-MANNITOL AS A FOOD INTAKE MODIFIER

This is a division of Ser. No. 910,698, filed Sept. 23, 1986, now U.S. Pat. No. 4,808,626.

BACKGROUND OF THE INVENTION

The present invention relates to the field of food intake modifiers, and more particularly to the field of modifiers that can be administered to increase or decrease mammalian food intake.

The physiology of the control of food intake is not well understood. Many cogent theories have been advanced based on data and observation. Several of these theories are discussed in "Physiology of the Control of Food Intake", Kissileff et al, Ann. Rev. Nutr. 2:371–418 (1982); Russek "Current Status of the Hepatostatic Theory of Food Intake Control", Appetite 2:137–143 (1981); and Friedman et al, "The Physiological Psychology of Hunger: A Physiological Perspective", Physiological Review, 83(6):409–431 (1976). Notwithstanding the current knowledge in this area, the effect that the administration of any given substance will have upon a mammal's food intake is normally difficult if not impossible to predict in the absence of significant food intake data stemming from prior experience with that compound or substance.

The present invention relates in particular to the effects of 2,5-Anhydro-D-mannitol and its effect on the food intake behavior of mammals. 2,5-anhydro-D-mannitol is a known fructose analog. The literature contains several reports concerning the possible biochemical and/or metabolic effects of 2,5-anhydro-D-mannitol (hereinafter referred to as 2,5-AM). See Riquelme et al, "Mechanism of Action of 2,5-anhydro-D-mannitol in Hepatocytes", Journal of Biological Chemistry, 259(8):5115–5123 (April 25, 1984); Stevens et al, "2,5-Anhydro-mannitol Inhibits Gluconeogenesis from Dihydroxyacetone in Rat Hepatocytes", Fed. Proc. 42 (Part II) Abstract No. 2384 (1983); Stevens et al, "2,5-Anhydro-D-mannitol Inhibits Glycogenolysis In Isolated Rat Hepatocytes", Fed. Proc. 40 (Part I) Abstract No. 3479 (1981); Hanson et al, "Hypoglycemic Effect of 2,5-anhydro-D-mannitol", Fed. Proc. 42 (Part II), Abstract No. 1453 (1983); Raushel et al, "The Substrate in Anomeric Specificity of Fructokinase", Journal of Biological Chemistry, 248 (23):8174–8177 (Dec. 10, 1973); Riquelme et al, "Inhibition by 2,5-anhydro-mannitol of Glycolysis in Isolated Rat Hepatocytes and in Ehrlich Ascites Cells", Proc. Natl. Acad. Sci. USA, 82:78–82 (Jan. 1985); Riquelme, "Regulation of Carbohydrate Metabolism by 2,5-anhydro-D-mannitol", Proc. Natl. Acad. Sci. USA, 80:4301–4305 (July, 1983); and Hanson et al, "Inhibition of Gluconeogenesis and Glycogenolysis by 2,5-anhydro-D-mannitol", Journal of Biological Chemistry, 259 (1):218–223 (Jan. 10, 1984). While most of these papers address the effect of 2,5-AM at cellular and intracellular levels, please note that Hanson et al (1984) discloses the administration of 2,5-AM to fasting mice and rats. Hanson et al fails to report any food intake data, nor does Hanson suggest what effect, if any, 2,5-AM might have in altering food intake.

Notwithstanding what is known about 2,5-AM and a variety of other substances, a need still exists for substances to treat overeating or obesity, and/or anorexia or other conditions exhibiting a reduced appetite.

SUMMARY OF THE INVENTION

The present invention provides a novel method for altering the food intake of a mammal comprising administering 2,5-anhydro-D-mannitol to said mammal in an amount sufficient to alter the food intake of said mammal. A preferred embodiment of the method comprises identifying the diurnal feeding and fasting periods of said mammal. (Fasting is defined as a period of 2 or more hours without food or with food restricted.) If an increase in food intake is desired, said mannitol is administered from up to two hours in advance of that fasting period to up to two hours from the expected conclusion of that fasting period to increase food intake during that fasting. If it is desired to reduce food intake, said mannitol is administered within two hours in advance of the onset of the identified diurnal feeding period to decrease the food intake during that period. The subject method also applies to mammals having irregular feeding habits, such as anotoxic mammals. The subject method preferably administers at least 50 mg/kg of said mannitol to said mammal, more preferably 100–800 mg/kg, although the lower and upper limits of administration have not yet been determined. The dosages were determined with rat tests, and those skilled in the art will recognize that the exact dosages for other mammals may differ.

Quite surprisingly, applicants have found that, depending upon the time of administration with respect to the mammal's feeding schedule, be it diurnal or irregular, the subject mannitol may either increase or decrease food intake. Such administrations have been found to be effective when administered by intragastric, intraperitoneal, or intravenous routes.

It is not presently understood why the subject mannitol exhibits the observed effect on food intake. While some of the results reported herein are consistent with in vitro studies suggesting that the phosphorylated products of 2,5-AM interfere with carbohydrate metabolism, the observed effect on food intake could not have been predicted from those studies. It is currently theorized that the increase in hunger during fasting periods, when the mammal relies on its stored sources of fuels, probably reflects inhibition of gluconeogenesis and glycogenolysis. The decrease in hunger during feeding periods, when the mammal utilizes exogenous fuels, probably reflects 2,5-AM induced enhancement of glycolysis. The administration of 2,5-AM thus holds promise as an orally-effective, peripherally-acting fructose analogue that may have therapeutic and other applications as a modulator of food intake when prescribed for a variety of different conditions.

Accordingly, a primary object of the present invention is the provision of a method of food intake modification to selectively increase or decrease mammalian food intake.

This and other objects of the present invention will become apparent from the following, more detailed description.

DESCRIPTION OF THE PREFERRED EMBODIMENTS

Figure 1:
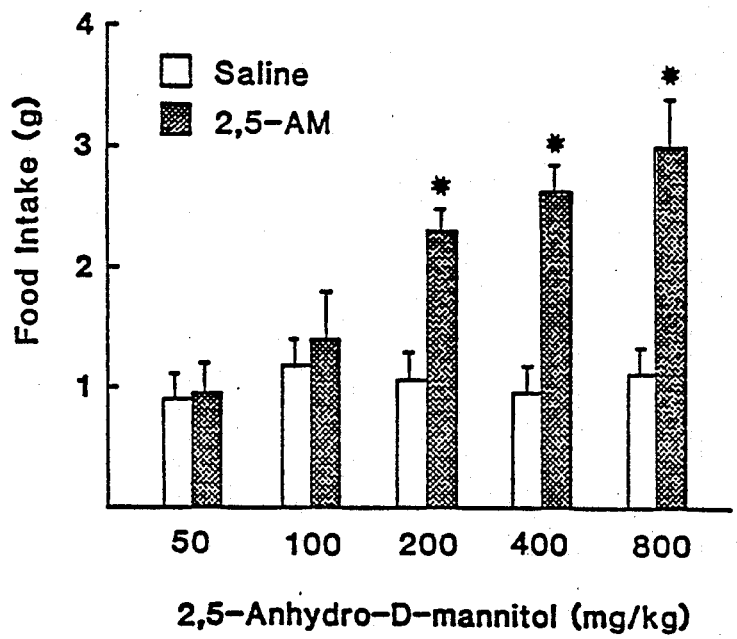
FIG. 1 is a bar chart showing food intake during the two hours after intragastric administration of 2,5-anhydro-D-mannitol (2,5-AM) during the day, asterisks indicating that P is less than 0.05 relative to the saline control.

The present invention provides a novel method of modifying the appetite of mammals by feeding 2,5-anhydro-D-mannitol to treat overeating, obesity or anorexia. In treating overeating or obesity, the subject material, a fructose analog referred to herein as 2,5-AM, is administered at or within two hours of an identified feeding period (mealtime) to depress the appetite. In treating anorexia or other conditions exhibiting a reduced appetite, the subject material is administered within up to two hours from the beginning of through two hours from the end of an identified fasting (between meals). Accordingly, depending upon the time of administration, the subject material accelerates growth or fosters a loss or gain of body weight and/or fat content. Although the feeding or fasting periods are preferably determined by identifying the diurnal feeding schedule of a mammal on a regular feeding schedule, the present method has applicability to determined feeding or fasting periods of irregular schedules as well, such as those of anorexic mammals.

2,5-AM is a fructose analog synthesized using published methods from glucosamine hydrochloride. As part of an on-going project to identify the metabolic controls of food intake, it has been found that this sugar administered to rats modifies food intake in a manner which indicates its use as an appetite depressant or stimulant depending on when it is given or taken relative to periods of feeding or fasting, respectively. The potency, sweet taste and oral effectiveness suggests that 2,5-AM could be used in food or beverages as well as in pharmaceutical media or vehicles towards these purposes. 2,5-AM can be used alone or along with other methods in the treatment of overeating, obesity or anorexia.

In order to achieve the intended effect, it is first necessary to determine the feeding patterns, and more particularly, the next feeding or fasting period, of the mammal whose food intake is to be altered. Preferably, the diurnal feeding pattern of a mammal on a regular feeding schedule is determined. For most humans, the identification of diurnal feeding and fasting periods is fairly simple. This will normally consist of 2-4 mealtimes per day between which are fasting periods of various durations. Other mammals also have identifiable feeding and fasting periods. Rats are nocturnal, normally fasting during the day, and depending upon the availability of a food source, feeding relatively continuously throughout the night. Dogs and cats similarly have identifiable feeding and fasting periods, which may vary somewhat from animal to animal, as have other mammals, such as cows, horses, sheep and other livestock. To demonstrate the effectiveness of the present invention, the following examplary tests were performed:

METHODS

Synthesis of 2,5-Anhydro-D-mannitol 2,5-Anhydro-D-mannitol was prepared according to the method disclosed in Horton, D., and Philips, K.D., *Methods in Carbohydrate Chemistry*, Vol. 7, 1976, 68–70, and Piper, I.M., MacLean, D.B., Kvarnstrom, I.K., and Szarek, W.A., *Can. J. Chem.*, 61, 1983, 2721–2728.

2,5-AM was administered in aqueous solution in a volume of 2 ml/kg body weight, except for the 800 mg/kg dose, which was dissolved in 1 ml/kg. Equal volumes of isotonic saline served as a control.

Subjects and Maintenance

All studies used male Sprague Dawley CD rats (Charles River, Wilmington, MA). They were housed individually in stainless steel cages and maintained at approximately 21° C. on a 12:12 hour light/dark cycle (lights off at 2:00 or 3:00 pm). Powdered Purina Rat Chow (#5001) and tap water were freely available unless otherwise noted.

Procedure

Rats were given at least ten days to adapt to vivarium conditions before tests began. They also received 1–4 mock intragastric intubations, consisting of insertion of a 3 in x 16 g curved intubation needle, to adapt them to the handling involved with intragastric administration.

Two experiments that examined the relationship between dose of 2,5-AM and food intake were conducted in parallel. The rats were intubated in one experiment (n=10; 358–409 g) in the middle of the light period and in the other (n=11; 342–387 g) at the beginning of the dark period. Ascending doses of 2,5-AM were given (50, 100, 200, 400, and 800 mg/kg). Each dose had its own saline control intubation. This was given according to a counterbalanced design on the preceding or proceeding day for the lowest three doses, and 48 hours later or earlier for the highest two doses. Each pair of saline and 2,5-AM intubations was separated from the following pair by at least three days. Food intake (to the nearest 0.1 g, corrected for spillage) was measured hourly for 4 hours and then daily.

After several weeks, the 10 rats used for the daytime dose-response experiment were used in an additional experiment that examined whether 2,5-AM given during the day could influence the intake of a non-nutritive saccharin solution. The rats (now weighing (454–586 g) were given three days exposure to ad libitum 0.2% sodium saccharin (Sigma Chemical Co., St. Louis, MO) dissolved in tap water to familiarize them to the sweet solution. Five hours before lights off on the test day, food was removed and half the rats were intubated with 400 mg/kg 2,5-AM and the others with saline. Saccharin intake (ml) was recorded hourly for 7 hours and at 24 hours, when food was returned. After four days, a further three days familiarization with saccharin was allowed and the rats were retested with the alternative solution intubated.

A comparison of intragastric and intraperitoneal administration of 2,5-AM was conducted in nine rats (434–542 g). These subjects received intragastric intubation or intraperitoneal injection of saline or 200 mg/kg 2,5-AM according to a counterbalanced crossed design, with each subject receiving each of the four combinations at 48 hour intervals. Administration of saline or 2,5-AM was performed in the middle of the light period, and food intake was recorded hourly for 4 hours and at 24 hours.

The relationship between the effects of 2,5-AM on blood metabolites and on feeding during the day was examined in 10 rats (411–481 g). These subjects were intubated with 200 mg/kg 2,5-AM or saline in the middle of the light period. At the same time their food was removed for 90 minutes. Immediately before food was returned, a 200,$\mu$ blood sample was collected from the tip of the tail in heparinized tubes. Food intake was measured at 1, 2, 3, and 4 hours. One week later, the procedure was repeated so that the rats previously given saline received 2,5-AM and those given 2,5-AM received saline.

Blood was centrifuged to obtain plasma. Glucose was analyzed using a Beckman Glucose Analyzer II (glucose oxidase method). Free glycerol, free fatty acids, triglycerides and total ketone bodies were determined by enzymatic procedures with fluorometric detection.

As all experiments used within subject designs, statistical tests used dependent-measures analyses. The results of metabolic assays were analyzed by t-tests for each metabolite. Food and saccharin intake data were analyzed by analysis of variance with treatment (saline vs. 2,5-AM) and measurement period (1, 2, 3, 4 hours) as factors. The dose-response experiments contained an additional factor of dose (50, 100, 200, 400, 800 mg/kg) in the analyses. Cumulative food and saccharin intake data were also compared when these appeared informative. If initial analyses were significant post hoc t-tests were conducted to discover significant differences between individual means. Probability cut-offs for significance were set at the $P$ less than 0.05 level.

RESULTS

2,5-Anhydro-D-Mannitol and Food Intake Dose-Response

Daytime Tests. The time of administration influenced the effect of 2,5-AM on food intake. During the first two hours after administration of 2,5-AM in the middle of the day, rats ate significantly more food than they did after saline administration, (1st hour, $F(1,9) =15.62$, $P$ less than 0.005; 2nd hour, $F(1,9) =9.68$, $P$ less than 0.05; cumulative 2 hours, $F(1,9) =20.78$, less than 0.005). During the 3rd and 4th hours there was no significant influence of 2,5-AM, although cumulative intakes following 2,5-AM remained significantly elevated ($F(1,9) =8.57$, $P$ less than 0.05; $F(1,9) =5.22$, $P$ less than 0.05, respectively). An interaction of dose with 2,5-AM treatment was present in the 2nd cumulative hour intakes, $F(4,36) =6.87$, $P$ less than 0.001, but not at other times, suggesting that the effects of 2,5-AM during the daytime tests were limited to about 2 hours duration. Doses of 2,5-AM greater than 100 mg/kg significantly increased food intake relative to both saline and the lowest two 2,5-AM doses (FIG. 1). Additionally, 800 mg/kg 2,5-AM increased food intake significantly more than did 200 mg/kg 2,5-AM, suggesting that 2,5-AM produces a dose-related increase in food intake when given during the day.

Food intakes during the 4–24 hours after daytime administration of the two highest doses of 2,5-AM were significantly decreased relative to saline controls (400 mg/kg; saline $=23.6$ $+1.02$, 2,5-AM $=18.0$ $+0.87$ g), but the lower doses did not influence 4–24 hour intake. The decrease seen with the 400 and 800 mg/kg doses was not simply compensation for the higher initial intakes, as cumulative 24 hour intakes were also significantly reduced by these doses (400 mg/kg; saline $=27.0$ $+0.84$, 2,5-AM $=23.9$ $+1.02$ g; 800 mg/kg; saline $=26.6$ $+1.02$; 2,5-AM $=21.4$ $+0.75$ g). There were no effects of 2,5-AM lasting more than 24 hours after administration.

Figure 2:
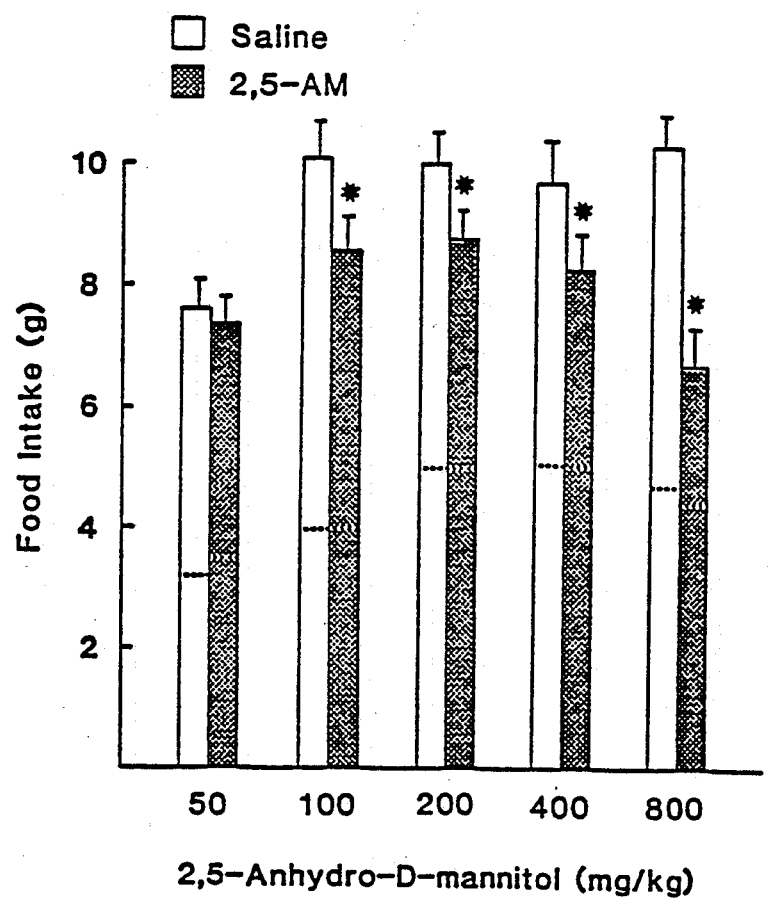
FIG. 2 is a bar chart similar to FIG. 1 illustrating food intake during the four hours after intragastric administration of 2,5-AM at the start of the dark period, horizontal dotted lines separating hours 1-2 from hours 3-4, asterisks again indicating that P is less than 0.05 relative to saline for both the 2-4 hour intakes and the cumulative four hour intakes, note being taken that 2,5-AM was ineffective during the first two hours after administration.

Nighttime Tests. When 2,5-AM was given at the start of the dark period, its effect was to decrease food intake. This was apparently a delayed response as there was no influence of 2,5-AM on feeding during the first 2 hours of the dark period (FIG. 2). On the other hand, 2,5-AM significantly reduced food intake during the 3rd hour, $F(1,10) =14.98$, $P$ less than 0.005, and this was also reflected in 3rd and 4th hour cumulative food intakes, $F(1,10 =16.98$, $P$ less than 0.005 and $F(1,10) =21.0$, $P$ less than 0.005, respectively (FIG. 2). A dose-response relationship was present at each of these times: For example, cumulative 4 hour food intakes were unaffected by 50 mg/kg 2,5-AM relative to its saline control (or an average of all saline control data). The four higher doses all significantly decreased food intake relative to saline, and the 800 mg/kg dose decreased intake significantly more than did the 100,200 or 400 mg/kg doses ($F4,40) =4.04$, $P$ less than 0.01 for the interaction).

As was the case with daytime administration of 2,5-AM, the 400 and 800 mg/kg doses significantly decreased 24 hour cumulative intake relative to saline controls (400 mg/kg; saline = $28.9$ $+1.13$, 2,5-AM $=22.4$ $+1.21$ g; 800 mg/kg; saline $=26.6$ $+0.84$, 2,5-AM $=17.9$ $+1.41$ g). There were no effects of the lower doses at 24 hours, or of any dose at 48 hours after 2,5-AM administration.

Influence of 2.5-Anhydro-D-mannitol on Saccharin Consumption

Figure 3:
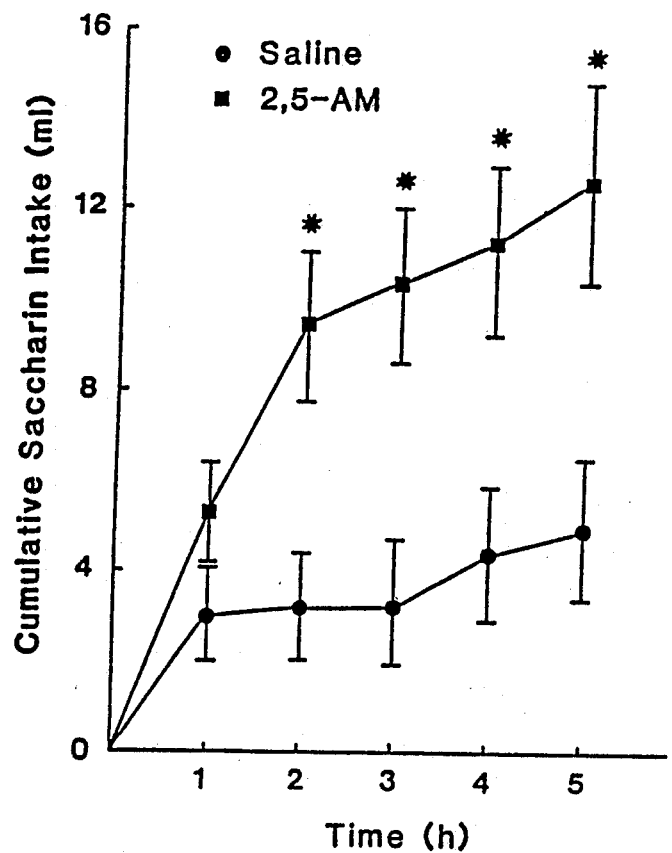
FIG. 3 is a graph showing intake of 0.2% saccharin solution by rats given 400 mg/kg of 2,5-AM during the day, food being unavailable during the tests, asterisks that P is less than 0.05 relative to the saline control.

Rats given 400 mg/kg 2,5-AM during the day drank significantly more saccharin in the following 5 hours than they did after saline administration, $F(1,9) =8.37$, $P$ less than 0.05. As was the case with daytime food intake, the increase was confined mostly to the first 2 hours, but was maintained in cumulative intakes for the remaining 3 hours of the light period (FIG. 3). During the first 2 hours of the dark, when saccharin intake was also recorded, rats given 2,5-AM 5 hours previously consumed similar quantities of saccharin (saline $=20.9$ $+5.14$; 2,5-AM $=17.0$ $+5.58$ ml/2 hours). There was also no significant difference in 24 hour saccharin intakes of saline- and 2,5-AM-treated rats.

Intragastric and Intraperitoneal Administration of 2,5-Anhydro-D-mannitol

Figure 4:
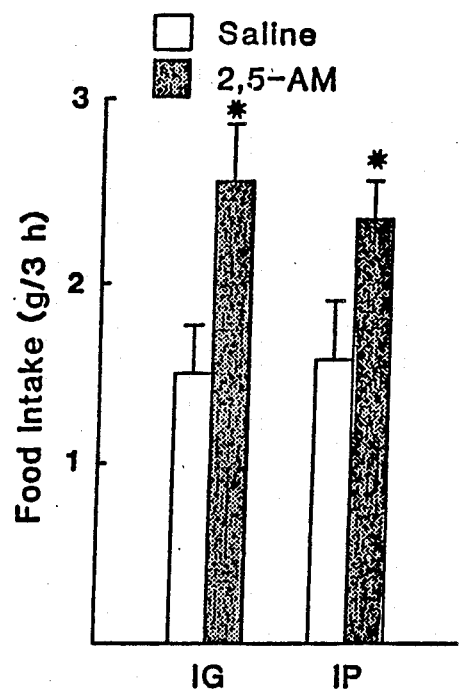
FIG. 4 is a comparison of three hour food intakes after intragastric (IG) or intraperitoneal (IP) administration of 2,5-AM during the day, showing that the two routes were equally effective in increasing food intake at all time periods, the asterisks again indicating that P was less than 0.05 relative to the saline control.

The results of intragastric intubation and intraperitoneal injection of 200 mg/kg 2,5-AM essentially replicated those seen in the daytime dose response curve (see above): Both routes of 2,5-AM administration produced a significant increase in food intake during the 1st and 2nd hour that were maintained in 3rd and 4th hour cumulative intakes (e.g., 4 hour cumulative food intake, $F(1,8) =7.50$, $P$ less than 0.05; FIG. 4). During the second cumulative hour there was a significant tendency for rats given intraperitoneal treatments to eat more than when they were tested with intragastric treatments, $F(1,8) =9.71$, $P$ less than 0.05; however, whichever route of administration was used, the increase in food intake produced by 2,5-AM was statistically similar (all interactions; F's less than 1.50).

Metabolic Measures

Table 1 shows the blood metabolite levels found 90 minutes after rats were given 200 mg/kg 2,5-AM in the middle of the day. 2,5-AM significantly decreased blood glucose, $t(9) = 4.51$, P less than 0.01, increased blood ketone bodies, $t(9) = 3.69$, P less than 0.01 and had no influence on triglycerides.

TABLE 1

Metabolic and feeding responses to 200 mg/kg 2,5-anhydro-D-mannitol given during the day.

| Measure | Saline | 2,5-AM |
|---|---|---|
| Metabolites (mM) | | |
| Glucose | 6.85 + 0.15 | 5.72 + 0.19* |
| Ketones | 0.11 + 0.01 | 0.18 + 0.01* |
| Triglycerides | 1.60 + 0.15 | 1.62 + 0.17 |
| Food Intake (g) | | |
| 1 hour cumulative | 1.37 + 0.40 | 2.77 + 0.47 |
| 2 hour cumulative | 2.13 + 0.22 | 3.20 + 0.45* |
| 3 hour cumulative | 2.75 + 0.28 | 4.03 + 0.45* |

Notes:
*P less than 0.05 relative to saline. Blood was taken 90 minutes after 3,5-anhydro-D-mannitol (2,5-AM) administration When food was returned after blood sampling, rats given 2,5-AM ate significantly more than they ate after saline. This increase was significant during the 2nd and 3rd cumulative hours, $(F(1,9) = 5.56$, P less than 0.05, $F(1,9) = 7.65$, P less than 0.05, respectively; Table 1), but not during the first hour, perhaps because of the stress of the blood sampling procedure.

Conclusion

Accordingly, it will be seen that a novel method of altering the food intake of a mammal is provided which is effective to selectively increase or decrease the amount of food consumed by that mammal, depending upon the time of administration of 2,5-AM relative to the determined feeding or fasting schedule of the mammal.

We claim:

1. A method of altering the food intake of mammal, comprising administering 2,5-anhydro-D-mannitol to said mammal in an amount and at a time effective to alter the food intake of said mammal.

2. The method of claim 1 wherein said administering comprises administering at least 50 mg/kg of said mannitol to said mammal at a time during the mammal's normal feeding cycle.

3. The method of claim 1 comprising intragastric administration of said mannitol.

4. A method of altering the food intake of a mammal comprising intraperitoneal administration of 2,5-anhydro-D-mannitol to said mammal in an amount effective to alter the food intake of said mammal.

5. The method of claim 1 wherein said food intake of said mammal is altered by increasing said food intake.

6. The method of claim 1 wherein said food intake of said mammal is altered by decreasing said food intake.

* * * * *